United States Patent [19]
Schwarz

[11] Patent Number: 6,117,415
[45] Date of Patent: Sep. 12, 2000

[54] TOOTHPASTE COMPRISING BIOADHESIVE SUBMICRON EMULSION FOR IMPROVED DELIVERY OF ANTIBACTERIAL AND ANTICARIES AGENTS

[75] Inventor: Joseph Schwarz, North York, Canada

[73] Assignee: AlphaRx Inc., Richmond Hill, Canada

[21] Appl. No.: 09/328,268

[22] Filed: Jun. 17, 1999

[51] Int. Cl.[7] ............................... A61K 7/16; A61K 7/22
[52] U.S. Cl. ................................. 424/49; 424/54
[58] Field of Search .......................... 424/49–58

[56] References Cited

U.S. PATENT DOCUMENTS

| | | |
|---|---|---|
| 3,475,533 | 10/1969 | Mayrand . |
| 3,574,824 | 4/1971 | Echgandian . |
| 3,705,940 | 12/1972 | Kirchgassner . |
| 3,937,805 | 2/1976 | Harrison ..................... 424/52 |
| 4,971,788 | 11/1990 | Tabibi et al. ............... 424/49 |
| 5,130,122 | 7/1992 | Tabibi et al. ............... 424/49 |
| 5,192,531 | 3/1993 | Gaffar et al. ............... 424/52 |
| 5,401,496 | 3/1995 | Fitzig et al. . |
| 5,472,706 | 12/1995 | Friedman, II et al. . |
| 5,512,278 | 4/1996 | Mundschenic . |
| 5,744,155 | 4/1998 | Friedman et al. ............ 424/434 |
| 5,750,142 | 5/1998 | Friedman, III et al. . |
| 5,817,325 | 10/1998 | Sawan et al. .............. 424/411 |
| 5,849,311 | 12/1998 | Sawan et al. .............. 424/406 |

FOREIGN PATENT DOCUMENTS

| | | |
|---|---|---|
| 127677B1 | 8/1990 | European Pat. Off. . |
| 2249652B1 | 10/1976 | France . |
| 60-226806A2 | 11/1985 | Japan . |

OTHER PUBLICATIONS

Ilan et al. Pharm. Res. 13(7): 1083–1087 (MA–SME Mucoadhesive Submicron Emulsion), 1996.

Sjuestrom et al. J. Pharm. Sci. 82(6): 584–589 O/W Poern, 1993.

*Primary Examiner*—Shep K. Rose
*Attorney, Agent, or Firm*—Paul S. Sharpe; Marks & Clerk

[57] ABSTRACT

Toothpaste incorporating chlorhexidine bigluconate for improved adhesive onto the surface of the teeth. A second embodiment discusses the use of triclosan and in combination with sodium monofluorphosphate for use in the toothpaste.

13 Claims, No Drawings

TOOTHPASTE COMPRISING BIOADHESIVE SUBMICRON EMULSION FOR IMPROVED DELIVERY OF ANTIBACTERIAL AND ANTICARIES AGENTS

FIELD OF INVENTION

The present invention relates to dental hygienic treatment and more particularly, the present invention relates to a submicron oil-in-water emulsion for prolonged local delivery of selected antibacterial compounds, especially chlorhexidine and chlorhexidine salts, quaternized alkylammonium derivatives, and triclosan, and additionally anticariotic compounds, such as fluorides, especially sodium fluoride, sodium monofluorphosphate and aminofluorides.

BACKGROUND OF INVENTION

In the prior art, there are countless formulations of toothpaste/dentifrice, attributed for improving of dental hygiene of the user. The known formulations include various types and concentrations of antibacterial agents, surfactants, fluoride components, abrasives, polymers, salts, oxidants, flavor compounds and other useful components for user teeth. Nevertheless most of the toothpastes with antibacterial components show relatively short antiseptic action due to intensive cleaning of the treated surfaces in the mouth by saliva and rapid reduction of the concentration of active component below minimal inhibiting concentration (MIC). In order to prolong action of the antiseptics toothpaste formulation containing antiseptic triclosan and maleic anhydride-vinyl methyl ether copolymer for improvement of antibacterial action (U.S. Pat. No. 5,192,531) was developed. The anionic character of the polymer makes impossible the use of the potent cationic antiseptics in this formulation.

Chlorhexidine incorporation into toothpaste composition is a problematic task due to formation of insoluble precipitates with common anions. Some of such compounds are patented, (U.S. Pat. No. 3,937,805); this approach was unsuccessful due to significant loss of antiseptic activity.

U.S. Pat. No. 5,130,122, describes a dental composition comprising oil-in-water submicron emulsion for dental use with improved customer properties. Although useful, this formulation has a relatively short retention time and rapid elimination from the mucous surfaces at the application. Sodium lauryl sulfate, needed for submicron emulsion preparation can cause irritation in gums and palate and is incompatible with cationic antibacterial substances, e.g., chlorhexidine salts or alkylammonium derivatives.

Another approach to extend the action of different agents is demonstrated in U.S. Pat. No. 5,744,155, where each droplet of the submicron emulsion is coated with polymer possessing pronounced mucoadhesive properties. Interaction of the polymer layer with mucosal surface leads to prolonged presence of the drug loaded lipid particle on the surface thus increasing time for local release of active compounds.

The present invention provides a pleasant tasting toothpaste composition providing long acting antibacterial and/or anti-caries action and method for its preparation.

SUMMARY OF INVENTION

One object of one embodiment of the present invention is to provide a toothpaste composition, comprising:
a physiologically acceptable oil, the oil composed of submicron particles;
a bioadhesive polymer coated on the submicron particles; and
at least one antibacterial compound.

A further object of one embodiment of the present invention is to provide a toothpaste composition, comprising:
a physiologically acceptable oil, the oil composed of submicron particles and present in an amount from between 0.1% and 50% by weight of the composition;
a bioadhesive polymer coated on the submicron particles in an amount from between 0.1% and 1.5%;
at least one antibacterial compound in an amount from between 0.1% and 5% by weight; and
filler material in an amount to 100%.

Since the active antiseptic component is entrapped into finely dispersed oil phase, its concentration in water is lower, thus unpleasant taste is significantly decreased. Moreover, chlorhexidine in submicron emulsion demonstrates less staining because reduced interaction of the oil droplets with tooth dentine and enamel. The bioadhesive coating of the tiny oil particles, charged with chlorhexidine or triclosan leads to significant prolongation of the drug presence on the mucous surfaces of the mouth, providing extended release of the antiseptic and flavor components.

The oil component of the emulsion can be chosen from many physiologically acceptable hydrophobic liquids, such as vegetable oils (soya bean, corn, sunflower, coconut, olive, jojoba, etc.), fish or animal oils, synthetic components—alcanes, squalane, paraffines, mineral oil, mono- and diol esters (propylene glycol caprylate, isopropyl myristate, dioctyl sebacate, lauroglycol) and glycerides (medium chain triglycerides), polymers—polysiloxanes, polyfluoralcanes, etc. The lipid component is preferably selected from long chain triglycerides (LCT, soya bean oil), medium chain triglycerides (MCT), alcanes (squalane) and esters (isopropyl palmitate, propyleneglycol dicaprylate). Concentration of the oil phase can vary from 0.1 to 50%, preferably from 1 to 20%, most preferably from 5 to 10%.

Surfactants, suitable for emulsifications, include most of the compounds, known to those skilled, such as sorbitan derivatives (Tween™, Span™), mono-, di- and polyglycerides, sugar derivatives (sucrose mono- and distearates), polyethylene glycol esters and ethers, polyethylene and polypropylene glycol block copolymers (Pluronic, Poloxamer), polyethoxylated oils (Cremophor), vitamins (Tocopherol succinate polyethyleneglycol, TPGS) and alkylphenoles (Triton, Tyloxapol), phosphatidylcholines and analogs (egg and soya lecithin), amphoteric (lauryl sarcosinate, cocoamphodiacetate, Miranol) and many others. All these compounds are generally recognized as safe and widely used in the pharmaceutical and food industries. Surfactants can be used either alone or in a mixture to obtain the desired emulsifying properties.

The surfactants may be selected from polyethoxylated sorbitan esters (Tween™), vitamins (ascorbyl palmitate, TPGS), sugar esters (sucrose stearate), polyethylene-polypropylene glycol copolymers (poloxamer), phosphatidylcholines (lecithin) and amphoterics (lauryl sarcosinate). The concentration range of the surfactant can vary from 0.01 to 10%, preferably from 0.1 to 5% more preferably from 0.2 to 2.0%.

Regarding the bioadhesive polymer used for oil droplet coating, this may be selected from wide variety of natural, synthetic or semi-synthetic products. Some illustrative examples include crosslinked polyacrylic acid (Carbopol™), carboxymethyl cellulose sodium salt (Na-CMC), hydroxypropylmethylcellulose (Methocel™), hyaluronic acid, alginic acid, chitosan, pectin, locust bean gum, xantan gum, acacia gum. The most preferable polymers are Carbopol™, hydroxypropylmethylcellulose and xantan gum.

Preferable antibacterial compounds include chlorhexidine and chlorhexidine salts, such as bigluconate or diacetate, triclosan, cetylpyridinium chloride, benzalconium chloride and cetyltrimethylammonium bromide.

Preparation of the submicron emulsion with bioadhesive oil droplets is achieved using a high pressure homogenizer. Different types of such equipment can be used such as Microfluidizer, Gaulin, Avestin, Rainin, etc.

Generally speaking, at a first stage, a lipid phase is prepared by dissolution of the antibacterial component in the oil phase together with surfactant mixture, antioxidant and flavors component. Subsequently, the oil phase undergoes emulsification in a previously prepared water phase comprises diluted water solution of the bioadhesive polymer, using usual propeller or rotor-stator mixer. A coarse emulsion is obtained and treated by the high pressure homogenizer in order to obtain submicron emulsion, followed, if necessary, with pH adjusting.

Particle size in the emulsion depends on oil phase concentration, type and concentration of the surfactant and polymer and treatment intensity. Typically, for 5–10% oil phase, the particle size is between 50 and 200 nm, 10–20% oil phase results in 250–350 nm average diameter (measured by light scattering).

The prepared bioadhesive submicron emulsion including the antibacterial component can be mixed with water-soluble anti-caries compounds (e.g., sodium fluoride).

To prepare a toothpaste based on the bioadhesive emulsion viscosity modifiers, abrasives, sweeteners, humectants, preservatives and other minor components will be added and carefully mixed to obtain the composition with required properties. The paste can be packaged into suitable tubes and can be stored in ambient conditions for long periods of time.

In addition the toothpaste can include an anti-caries agent, selected from fluoride compounds, such as sodium fluoride (for chlorhexidine containing compositions) in concentrations between 0.1 to 0.5%, preferably between 0.20 to 0.23% by weight of the said toothpaste, or sodium monofluorphosphate for triclosan containing compositions, in concentration from between 0.5 to 1.0%, preferably between 0.76 and 0.84% by weight of the said toothpaste.

Viscosity regulating agents can be selected according to prior art from the group of water-soluble polymers (Na-CMC for triclosan formulations, HPMC for chlorhexidine formulations) or colloidal silicon dioxide (fumed silica, Aerosil, Cab-O-Sil).

Precipitated calcium carbonate, silicon dioxide, calcium phosphate, sodium polyphosphate and other compounds can be used as abrasive components.

Peppermint oil, spearmint oil, menthol, clove oil, lemon oil, other essential oils and artificial flavors can be used as flavor agents. Due to the hydrophobic nature of these components most of the flavor substance will be entrapped into the oil particles of submicron emulsion thus providing prolonged presence in the mouth and a feeling of freshness.

Vitamins (vit. A-retinol, vit. E-tocopherol, vit. K-naphtoquinone, vit. C-ascorbyl palmitate) and other biologically active compounds may also be added to the toothpaste.

The practice of this invention is illustrated by, but not limited to the following examples of the toothpaste compositions and preparation of the said formulations. All ratios are in weight parts unless is otherwise mentioned.

DETAILED DESCRIPTION OF THE PREFERRED EMBODIMENTS

EXAMPLE 1

Bioadhesive submicron emulsion based toothpaste with 1% chlorhexidine bigluconate.

As a first example of the first formulation, the toothpaste composition contains chlorhexidine bigluconate in amount of 1% by weight basis, i.e., 5.2% of 20% solution of chlorhexidine bigluconate. The oil phase comprises 4.5% medium chain triglycerides (MCT oil, Crodamol™ TGCC, manufactured by Croda) and 0.5% soya lecithin (Leci PC 35, Lucas Meyer), weight ratio between lecithin and oil phase is 1:10. To prevent lecithin oxidation an antioxidant, alpha-tocopherol acid hemisuccinate, has been found to be useful in the present formulation. It was added in amount of 0.02%.

As surfactant with high HLB value polysorbate-20 (Tween-20™, polyethoxylated sorbitan monolaurate, manufactured by Croda) in amount 1% was employed.

In order to provide prolonged retention of the formulation, a mucoadhesive polymer is employed according to this embodiment in the present invention. The mucoadhesive polymer, compatible with chlorhexidine, is hydroxypropylmethylcellulose, manufactured by the Dow Chemical company and sold under the trademark METHOCEL E100M. This material has two functions: mucoadhesive properties development in concentration of 0.5%, and a total 1.5% was used for viscosity regulation.

Dibasic calcium phosphate was used as a mild abrasive and filler material in amount of 36%. The material may readily be substituted by calcium carbonate or silicon dioxide (milled zeolite).

Colloidal silicon dioxide manufactured by Cabot or Degussa was used as a binding agent and added in amount from between 0.5 to 5%, and preferably 1.8%.

Flavoring agents may be employed and as example, DL-menthol may be added in an amount of between 0.1 and 1.0% and preferably 0.2%. As an alternative, peppermint oil or wintergreen oil may be used.

Variations in the formulation include glycerol which can be substituted (partially or completely) with liquid polyethylene glycol (e.g., PEG-400) or propylene glycol.

For viscosity regulation, other non-ionic gel-forming polymers can be used instead of HPMC: hydroxyethylcellulose (HEC), hydroxypropylcellulose (HPC), methylcellulose. If instead of dry sorbitol (powder) 70% solution is used, the amount of added water must be recalculated according to the generic formulation.

Tween™ can be readily substituted by another suitable non-ionic surfactant, examples of which include PEG-32 stearate, Simulsol™, Cremophor™ EL-35, Tefose™, etc. It will be appreciated also that at least part of abrasive component can be replaced by Titanium dioxide (white pigment) to obtain white toothpaste.

| Toothpaste Composition of Example 1 | | | |
|---|---|---|---|
| Component | Type/grade | Manufacturer | % |
| Chlorhexidine bigluconate 20% solution | USP | | |
| contains: Chlorhexidine bigluconate | | | 1.04% |
| water | | | 4.16% |

-continued

Toothpaste Composition of Example 1

| Component | Type/grade | Manufacturer | % |
|---|---|---|---|
| Purified Water | USP/NF | | 32.84% |
| Glycerol | USP/NF | Henkel | 7.00% |
| Sorbitol powder | USP/NF | Roquette | 8.00% |
| MCT (Medium Chain Triglycerides) oil | Crodamol TGCC | Croda | 4.50% |
| alpha-Tocopherol hemisuccinate | Vitamin E acid succinate | Eastman | 0.02% |
| Lecithin (Leci PC 35P) | USP/NF | Lucas Meyer | 0.50% |
| Tween-20 ™ (Polysorbate-20) | USP/NF | Croda | 1.00% |
| Hydroxypropylmethylcellulose (HPMC) | Methocel E100M | Dow Chemical | 1.50% |
| Dibasic Calcium Phosphate dihydrate | NF | Mendell | 36.00% |
| Colloidal silicon dioxide (Cab-O-Sil 300) | USP/NF | Cabot | 1.80% |
| DL-Menthol or Peppermint oil | NF | FLUKA | 0.20% |
| Na Saccharinate | USP/NF | | 0.20% |
| Na Benzoate | NF | | 0.20% |
| Total | | | 100% |

In terms of preparation of 10 kg batch of the toothpaste, following to example, at first stage 2.5 g of the Methocel E100 M was dispersed in 500 gram of purified water. This mixture was heated to 90° C. and stirred until the polymer was completely hydrated. Two kilograms of cold water was added and stirred until complete dissolution. Glycerol, in an amount of 700 g, was added and stirred until a homogenous solution was obtained.

At a second stage of preparation, 50 g of lecithin and 2 g of vitamin E acid succinate and 20 g of peppermint oil or D,L-menthol were consequently added to 450 g of medium chain triglyceride oil (Crodamol TGCC) and stirred slowly until clear solution was prepared. After complete dissolution, 100 g of non-ionic surfactant Tween-20TM was added and stirred for homogenous dispersion. This oil phase was combined with 520 g of 20% chlorhexidine bigluconate solution followed by intensive stirring.

In a further stage, the product from the second stage described above was mixed with the material from the first stage, using a high speed rotor-stator type mixer (Ultra-Turrax®, Polytron®), Silverson™ or similar type arrangements) until a homogenous emulsion was formed. The formed emulsion was treated with high pressure homogenizer (Gaulin®, Microfluidizer®, Avestin® or similar) at predetermined pressure between 600 and 1200 bar. The emulsion was passed between one to three times through the homogenizer to obtain desired submicron emulsion. Sodium saccharine in amount of 20 g and 20 g of sodium benzoate and 800 g of Sorbitol were added to emulsion and stirred until completely dissolved.

In the final stage, 147.5 g of hydroxypropylmethylcellulose was dispersed in 784 g of water. This mixture was heated to 90° C. and mixed well until all the Methocel E100M was hydrated. The homogenized submicron emulsion was added to hydrated Methocel at room temperature and mixed until polymer was homogeneously distributed.

Dibasic calcium phosphate was gradually added to formed mixture in amount of 3600 g. The mixture was stirred well and then approximately 180 g of colloidal silicon dioxide were gradually added until desired viscosity is achieved. The latter number represents a variable amount, this may be adjusted during manufacture to reach desired viscosity of the paste. The viscous mixture was then passed through 60 mesh screen, degassed in vacuum to remove entrapped air bubbles and packaged.

EXAMPLE 2

A bioadhesive submicron emulsion based toothpaste with 0.3% Triclosan as antibacterial agent, and sodium monofluorphosphate as anti-caries additive for improved oral hygiene.

In this example, triclosan arranges as a part of a mixture as a component in amount from 0.1 to 1.0%, or most desirably 0.3%. Further, the triglyceride oil, an example of which is Myritol 318™ manufactured by Cospha-Henkel, was incorporated into the mix in amount from between 2.0 to 20%, and desirably 4.62%. Egg lecithin was used as additional emulgator, and high molecular weight caroxymethylcellulose was employed as bioadhesive polymer and also as viscosity regulating agent. Sorbitol was used as 70% solution.

Toothpaste composition for Example 2

| Phase | Component | Type | Manufacturer | % |
|---|---|---|---|---|
| A | Triclosan | USP/NF | | 0.30% |
| A | MCT oil | Myritol 318 | Cospha-Henkel | 4.62% |
| A | alpha-Tocopherol hemisuccinate | | Eastman | 0.02% |
| A | Lecithin (80% phosphatidylcholine) | E-80 | Lipoid | 0.50% |
| A | Tween-80 ™ (Polysorbate-80) | USP/NF | | 1.00% |
| A | Peppermint oil | | Flavorchem | 1.00% |
| B | Purified Water | | | 10.00% |
| B | Sorbitol 70% | NF | | 18.00% |
| B | Carboxymethylcellulose 9M31XF | NF | Hercules | 0.10% |
| C | Sorbitol 70% | | | 8.00% |
| C | Glycerol 96% | | Henkel | 8.20% |
| C | Carboxymethylcellulose 9M31XF | | | 0.90% |
| C | Dibasic calcium phosphate, dihydrate | | | 30.00% |
| C | Dibasic calcium phosphate, anhydr. | | | 16.00% |
| C | Sodium monofluorphosphate | | | 0.76% |
| C | Sodium sacharinate | | | 0.25% |
| C | Sodium benzoate | | | 0.10% |
| C | Sodium phosphate, tribasic | USP/NF | FLUKA | 0.25% |
| | Total | | | 100% |

Carboxymethylcellulose grade and amount can be adjusted according to desired paste final viscosity value. Polyacrylic acid (Carbomer, Carbopol™), Xantan gum (Keltrol), Hydroxypropylmethylcellulose (HPMC) and other polymers, such as hydroxyethylcellulose (HEC), hydroxypropylcellulose (HPC), methylcellulose can be used for viscosity regulation.

Tween-80™ can be replaced by another suitable non-ionic surfactant (PEG-32 stearate, Poloxamer, Simulsol, Cremophor, Tefose, etc.). In formulation with triclosan up to 80% of Tween™ can be replaced by sodium laurylsulfate (SLS) or sodium laurylsarcosinate or mixture thereof. pH of the toothpaste, if necessary, can be adjusted to desired value, using sodium triphosphate and/or monophosphate.

EXAMPLE 3

This example sets forth a toothpaste based on bioadhesive submicron emulsion with 1% chlorhexidine bigluconate and 0.22% sodium fluoride for oral hygiene. This formulation was prepared as example 1, but part of dibasic calcium phosphate was substituted with 0.22% sodium fluoride to achieve anti-caries properties.

EXAMPLE 4

This formulation represents submicron emulsion based clear gel for oral hygiene with cetylpiridinium chloride and sodium fluoride. It was prepared by the same method as Example 1, but lipid phase of the submicron emulsion is prepared of isopropyl palmitate and soya lecithin S-75, cetylpiridinium chloride employed as antibacterial agent, and abrasive silica was selected to prepare clear gel. Sodium fluoride is used as anti-caries agent.

| Toothpaste composition for Example 4 | |
|---|---|
| Component | % |
| Glycerin 96% | 16.5 |
| Isopropyl palmitate | 5.8 |
| Tocopherol PEG1000 succinate | 0.2 |
| Lecithin S-75 | 0.64 |
| Tween-20 ™ (Polysorbate-20) | 1.0 |
| Peppermint oil/Clove oil/Anise oil flavor mix | 1.0 |
| Purified Water | 5.0 |
| PEG-400 | 8.0 |
| Cetylpiridinium chloride | 1.0 |
| Colloidal silicon dioxide | 8.0 |
| Sorbitol 70% | 37.9 |
| Hydroxypropylmethylcellulose Methocel ® E15M | 0.4 |
| Abrasive silica (milled zeolite) | 14.0 |
| Sodium fluoride | 0.22 |
| Sodium saccharinate | 0.24 |
| Sodium benzoate | 0.1 |
| Total | 100.0 |

EXAMPLE 5

In this example, a toothpaste based on bioadhesive submicron emulsion with 0.3% of triclosan. This formulation was prepared as example 2, but the amount of carboxymethylcellulose 9M31XF was substituted with Carbopol 934P, and pH was adjusted to 6.0–6.5 to achieve optimal bioadhesive properties of the submicron emulsion.

The main advantage of bioadhesive submicron toothpaste is significantly extended presence of the active ingredients of the toothpaste in the mouth thus providing prolonged antiseptic action and better tooth protection. Secondly, most of the antibacterial substance, e.g., chlorhexidine, is located on the oil/water interface of the submicron emulsion, in accordance with thermodynamic properties and partition and free drug concentration in the water phase is significantly decreased. It leads to apparent improvement of the taste of such submicron emulsion compositions. Further, is connected with better penetration of submicron particles inside the surface layer of the oral mucose in the mouth. Flavor components, included in the oil droplets, better penetrate and supply better freshness in local application. Last, but not least factor is significantly lower teeth staining with chlorhexidine toothpastes based on submicron emulsion compositions. Formulation can be readily adjusted by those skilled in the art to numerous modifications, comprising different active components, flavors and another ingredients.

Although embodiments of the invention have been described above, it is not limited thereto and it will be apparent to those skilled in the art that numerous modifications form part of the present invention insofar as they do not depart from the spirit, nature and scope of the claimed and described invention.

I claim:
1. A toothpaste composition, comprising:
   a physiologically acceptable oil in water emulsion, composed of submicron particles;
   a bioadhesive polymer coating on each particle of said submicron particles; and
   at least one antibacterial compound of chlorhexidine or chlorhexidine salt.
2. The composition as set forth in claim 1, wherein said bioadhesive polymer is a mucoadhesive polymer.
3. The composition as set forth in claim 1, wherein said composition further includes at least one viscosity regulating agent selected from the group comprising colloidal silicon dioxide, carboxymethylcellulose, hydroxyethylcellulose, hydroxypropylcellulose, calcium carbonate, calcium bicarbonate; calcium phosphate, calcium monofluorophosphate, sodium carbonate, sodium bicarbonate and sodium phosphate.
4. The composition as set forth in claim 1, wherein said chlorhexidine salts comprise bigluconate, diacetate, acetate, chloride, dodecylsulfonate, steatate and palmitate.
5. The composition as set forth in claim 1, wherein said oil is selected from vegetable, fish or animal oils.
6. The composition as set forth in claim 1, wherein said oil is selected from synthetic and semi-synthetic compounds selected from the group comprising alcanes, squalane, paraffines, mono- and diol esters and glycerides.
7. The composition as set forth in claim 1, wherein particle size for a 5–10% oil phase is between 50 and 200 nm.
8. The composition as set forth in claim 1, wherein said oil is in a concentration of between 0.1% and 50% by weight.
9. The composition as set forth in claim 1, wherein said bioadhesive polymer is selected from the group comprising crosslinked polyacrylic acid, carboxymethyl cellulose sodium salt (Na-CMC), hydroxypropylmethylcellulose, hyaluronic acid, alginic acid, chitosan, pectin, locust bean gum, xanthan gum, acacia gum.
10. A toothpaste composition, comprising:
    a physiologically acceptable oil in water emulsion, composed of submicron particles and present in an amount from between 0.1% and 50% by weight of said composition;
    a bioadhesive polymer coating on each particle of said submicron particles in an amount from between 0.1% and 1.5% by weight;
    at least one antibacterial compound of chlorhexidine or chlorhexidine salt in an amount from between 0.1% and 5% by weight; and
    filler material in an amount to 100%.
11. The composition as set forth in claim 10, wherein said bioadhesive polymer is a mucoadhesive polymer.
12. The composition as set forth in claim 10, wherein said composition further includes at least one viscosity regulating agent selected from the group comprising colloidal silicon dioxide, carboxymethylcellulose, hydroxyethylcellulose, hydroxypropylcellulose, calcium carbonate, calcium bicarbonate; calcium phosphate, calcium monofluorophosphate, sodium carbonate, sodium bicarbonate and sodium phosphate.
13. The composition as set forth in claim 10, wherein said chlorhexidine salts comprise bigluconate, diacetate, acetate, chloride, dodecylsulfonate, steatate and palmitate.

* * * * *